US006036633A

United States Patent [19]

Hodge

[11] Patent Number: 6,036,633

[45] Date of Patent: Mar. 14, 2000

[54] DUAL INCUBATOR TEMPERATURE CONTROL SYSTEM

[75] Inventor: Colin G. Hodge, Columbia, United Kingdom

[73] Assignee: Datex-Ohmeda, Inc., Tewksbury, Mass.

[21] Appl. No.: 09/015,992

[22] Filed: Jan. 30, 1998

[51] Int. Cl.[7] .......................... A61G 11/00; A61G 10/00; A61B 5/00; A01G 23/10; G05D 23/00

[52] U.S. Cl. .............................. 600/22; 600/21; 600/549; 236/2; 236/3; 236/9 F; 236/94

[58] Field of Search ................................ 600/22, 21, 549; 236/3, 9 R, 9 A, 91 F, 2, 1 R, 91 D, 94, 91 R, 99 E; 237/3, 14

[56] References Cited

U.S. PATENT DOCUMENTS

| | | | |
|---|---|---|---|
| 3,335,713 | 8/1967 | Grosholz et al. | 600/22 |
| 4,034,740 | 7/1977 | Atherton et al. | 600/22 |
| 4,171,770 | 10/1979 | Mailander, Sr. | 237/3 |
| 4,429,829 | 2/1984 | Dutton | 236/78 B |
| 4,509,505 | 4/1985 | Mercey et al. | 600/22 |
| 4,572,427 | 2/1986 | Selfridge et al. | 236/3 |
| 4,701,415 | 10/1987 | Dutton et al. | 435/289 |
| 4,846,783 | 7/1989 | Koch et al. | 600/22 |
| 5,162,038 | 11/1992 | Wilker | 600/22 |
| 5,316,542 | 5/1994 | Koch et al. | 600/22 |
| 5,385,529 | 1/1995 | Koch | 600/22 |
| 5,415,618 | 5/1995 | Koch | 600/22 |
| 5,453,077 | 9/1995 | Donnelly et al. | 600/22 |
| 5,853,361 | 12/1998 | Kobayashi et al. | 600/22 |

*Primary Examiner*—Cary O'Connor
*Assistant Examiner*—Navin Natnithithadha
*Attorney, Agent, or Firm*—Roger M. Rathbun

[57] ABSTRACT

An infant incubator having a heating system that provides a flow of heated air into the infant compartment and which exhausts air from the infant compartment. A temperature sensor is located in the air inlet of the warm air into the infant compartment and another temperature sensor is located in the air outlet of the air from the infant compartment. The system thus monitors the temperature of the air to the infant compartment and the air from the infant compartment. By analyzing the temperatures from the inlet and the outlet the overall incubator heating system can be controlled and yet a further advantage is provided by using the temperature information to recognize a fault or deficiency in the incubator system.

1 Claim, 2 Drawing Sheets

DUAL INCUBATOR TEMPERATURE CONTROL SYSTEM

BACKGROUND

This invention relates to a system for controlling the internal temperature of an infant compartment within an infant incubator, and, more particularly, to a system that detects the temperature of the air at two locations in the overall heating system for the infant incubator to determine the temperature within the infant compartment as well as to derive other useful information concerning the operation of the heating system of the infant incubator.

There are, of course, many differing systems for controlling the temperature within an infant compartment of an infant incubator. Generally, the purpose of such systems is to provide accurate and reliable thermal regulation to the infant positioned within that infant compartment. As such, the infant incubator generally includes a heating system that provides a flow of heated air into the infant compartment to warm the infant. The temperature and/or flow of the warm air is closely regulated so that the internal conditions of the infant compartment are the desired conditions for that particular infant.

In carrying out such heating, various systems are in use or published that sense the air temperature within the infant compartment and use that temperature as input to the controller that operates the heating system. Other systems may sense the skin temperature of the infant, either as a control input or as a monitoring input as well as the sensing of various temperatures within the infant compartment. In general, there are many differing systems and locations for the sensing of temperatures used to control and/or monitor the conditions within the infant compartment and to insure that the heating system is operating within the expected parameters.

SUMMARY OF THE INVENTION

The present invention is based upon a system that uses two air sensors in carrying out the control and monitoring of the heating system that supplies the warm air to the infant compartment. One sensor is located in the inlet of warm air to the infant compartment and the other sensor is located in the outlet of air from the infant compartment. In the preferred embodiment, both of the air sensors have dual sensors, that is, there is a redundancy built in by having two thermistors in both the inlet and the outlet of the infant compartment.

By the use of air temperature sensors in the two selected locations, the air temperature within the infant compartment can readily be derived, however, additional information can be gleaned from the sensing of air temperatures at these locations.

For example, by sensing the temperature at both the inlet and the outlet to the infant compartment, one can determine whether the heating system is operating properly, that is, the system can detect the existence of a fault in the fan system or a fault in the heater itself.

As a further feature or advantage of the present invention, the incubator can operate with the temperature sensors in the inlet and outlet of the infant compartment and such location of he sensors can eliminate the normal use of a cutoff thermostat normally operable to cut off the incubator heater at a predetermined maximum temperature and also can eliminate the need for air flow sensors that are used in conventional infant incubators. As such, therefore, certain components of a infant incubator can simply be eliminated without compromising the safety of the infant incubator.

These and other improvements and features of the present invention will become better understood from the detailed description of the preferred embodiment set forth below taken in conjunction with the accompanying drawings.

DETAILED DESCRIPTION OF THE INVENTION

Figure 1:
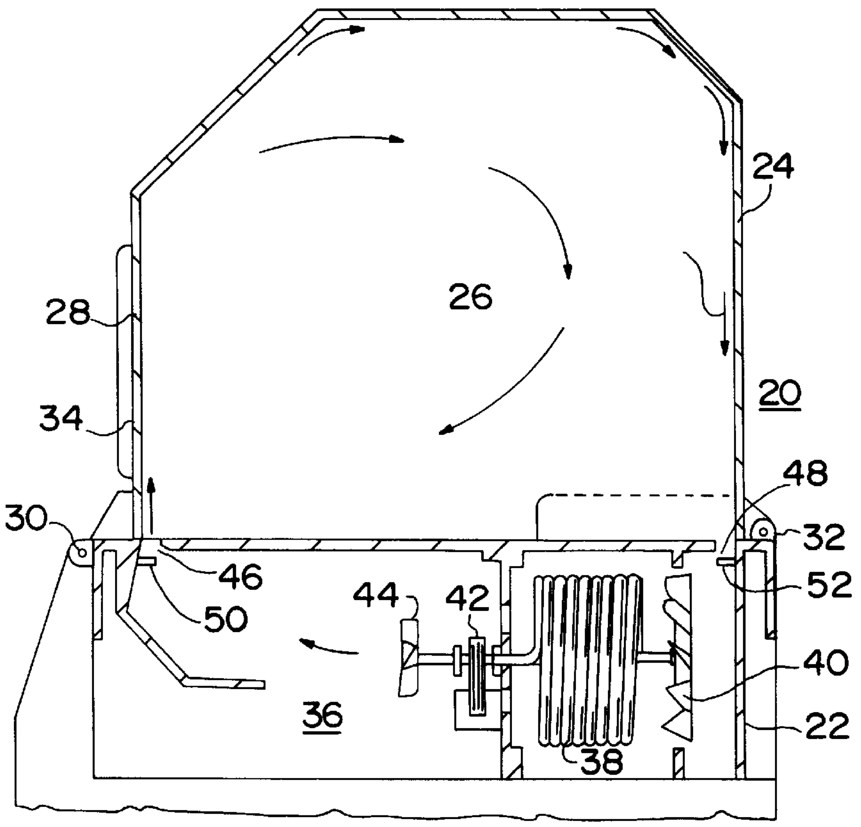
FIG. 1 is a side-sectional view of an infant incubator having incorporated therein, the present invention.

Referring now to FIG. 1, there is shown a cross sectional view of an infant incubator 20 and which includes a base 22, preferably of a rigid structural material including aluminum or plastic such as polycarbonate. The base contains much of the functioning mechanism for operation of the infant incubator 20 as will be later explained. The incubator 20 may be basically the same as shown and described in U.S. Pat. No. 4,936,824 of Koch et al and the disclosure of that patent is incorporated herein by reference.

A hood 24 overlies base 22 and encloses therein an infant compartment 26. Hood 24 is of a transparent material, preferably plexiglass, and has an access door 28 for the attending personnel to gain access to the infant contained within the infant compartment 26. The access door 28 can be pivotally connected to base 22 by means such as pins 30 or other alternate pivoting means can be used, such as piano type hinges. As can be noted the pins 30 are offset from the base of the access door 28 such that the pivot causes the access door 28, when opened, to be displaced from its normal position as will be later explained.

Hood 24 itself, may also be pivotally connected to the base 22 at the rear of the incubator 20 by means such as pivot 32 such that the entire hood 24 may be opened. The hood 24 may also include various other access openings such as a handhole 34.

A heater compartment 36 is contained within the base 22 and contains the heating means to heat and circulate the heated air through the infant compartment 26. The heating means may comprise a conventional heater 38 and a fan 40 that induces the air past heater 38 to heat the air which then enters the remaining part of the heater compartment 36. A fan motor 42 with a cooling fan 44 is used to power the fan 40. The warm air that is heated by the heater 38 is passed through an air inlet 46 to the infant compartment 26 and the heated flow of air thus circulates through the infant compartment 26 to provide warming to the infant that is contained within the infant compartment 26. Eventually, the heated air, somewhat cooled, reenters the heater compartment 36 in the base 22 through the air outlet 48.

Accordingly as can now be seen, the incubator 20 provides a stream of heated air from the base 22 that emerges into the infant compartment 26 through air inlet 46 and which then circulates through the infant compartment 26 and eventually reenters the base 22 through the air outlet 48. The heated flow of air thus gives up some of its heat during passage through the infant compartment 26 and thus is cooled somewhat as it passes through the air outlet 48 as opposed to its temperature where it enters the infant compartment 26 via the air inlet 46.

A temperature sensor 50 is located within or in close proximity to the air inlet 46 and a further temperature sensor 52 is located in or in close proximity to the air outlet 48. The sensors themselves maybe be conventional thermistors and which carry out the function of measuring the temperature of the air as it passes into the infant compartment 26 through the inlet 46 and again as the air passes out of the infant compartment 26 through the air outlet 48. The difference in temperatures is, therefore, an indication of the heat given up by the stream of heated air in the infant compartment 26 to warm the infant.

Figure 2:
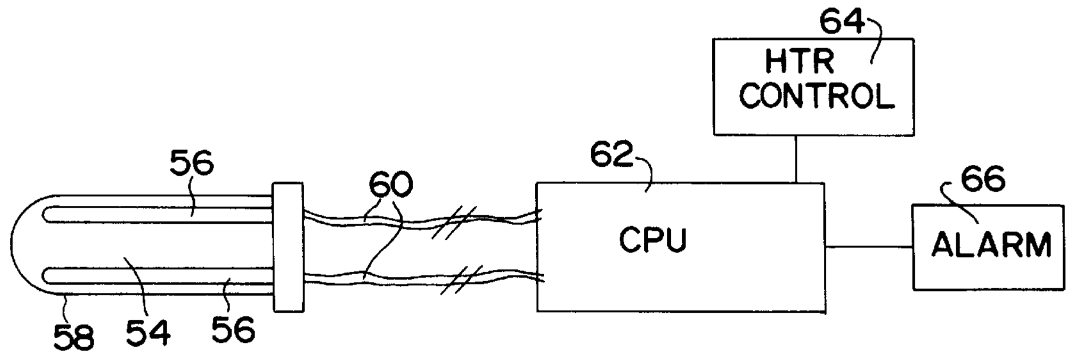
FIG. 2 is a schematic of a temperature sensor that is adapted to be used with the present invention.

Turning now to FIG. 2, in conjunction with FIG. 1, there is shown a schematic of a temperature sensor 54 that is usable with the preferred embodiment of the present invention. The temperature sensor 54 may be used as either or both of the temperature sensors 50 and 52 of FIG. 1 and comprised a pair of thermistors 56 contained within a sheath 58 of a good heat conducting material. As such, the temperature sensor 54 has basically a redundancy built in, that is, in the event of a failure of either of the thermistors 56 the other thermistor within the sheath 58 can be used to sense the appropriate temperature. Suitable wires 60 are used to connect the thermistors 56 to other portions of the control scheme, specifically to a central processing unit (CPU) 62 that receives the signals from the thermistors 56 indicative of the temperature sensed, in this case, in the air inlet 46 and the air outlet 58 of the incubator 20 shown in FIG. 1.

With the temperatures thus sensed at the air inlet 46 and the air outlet 48, the CPU 62 can readily calculate and determine the air temperature within the infant compartment 26 without resort to an actual air temperature sensor contained within the infant compartment 26 and can use that derived temperature to drive a heater control 64 to provide control to the heater 38 and/or to control the speed of the fan 40 to provide the desired amount of heat to the infant compartment 26.

As a further feature of having the air temperature sensors located to detect the temperature of the air passing into the infant compartment 26 and passing out of the infant compartment 26, various parameters relating to the overall integrity of the heating system can be ascertained, and, if the integrity is not in accordance with the desire of the user or the system itself, the CPU 62 can determine the deficiencies in the heating system and alert the user by means of an alarm 66 that may be audible and/or visually to alert the user that something is not working properly in the heating system.

As examples of the fault detection system, there is shown in FIGS. 3A–F, various curves showing the performance of the incubator 20 based on the detection of the temperatures in the air inlet 46 and the air outlet 48. In any of these examples, the various curves may be detected by the CPU 62 and appropriate messages provided by the alarm 66 as the particular deficiency is identified. Alternatively, the CPU 62 may merely contain, in storage, the anticipated curves of the performance of the incubator and an alarm signaled wherever the temperature curves divert from the norm. IN such case, the alarm system would not try to identify the particular deficiency but merely signify an alarm condition. As a further alternative, of course, the differing curves and the data they represent by the various deficiencies may be trained into the CPU 62 by means of a standard neural net system and the particular deficiency specifically identified to the user.

Figure 3A:
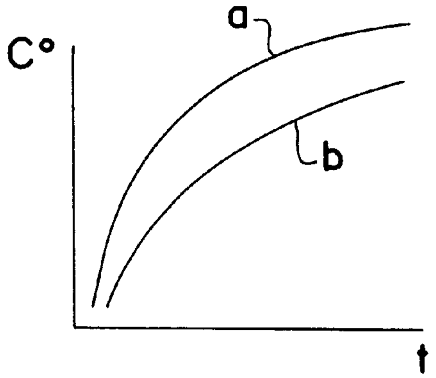
FIGS. 3A–F are a series of curves depicting various conditions of the present invention as applied to the system of FIG. 1.

Taking, therefore the specific curves of FIGS. 3A–F which are plots of temperature versus time, the curve of FIG. 3A represents the normal start-up and operation of the incubator 20. In all of the FIGS. 3A–3F, the curve "a" indicates a plot of the temperature sensed at the air inlet 46, that is, the temperature sensed by the temperature sensor 52 and the curve marked "b" is a plot of the temperature at the air outlet 48 and sensed by the temperature sensor 52. As can be seen, the normal temperature rise in FIG. 3A occurs with the temperature of the air in the air inlet 46 being at a higher temperature than the air passing from the infant compartment 26 through the air outlet 48 as would be expected.

Figure 3B:
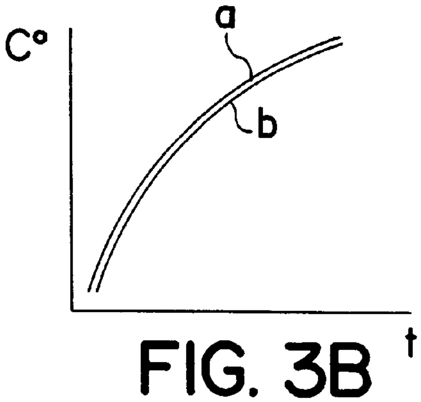

With FIG. 3B, however, an abnormal condition is sensed by the two temperature sensors 50 and 52. In FIG. 3B, the condition represented would be if the fan 40 were not operational and, as can be seen, the temperatures in the air inlet 46 and the air outlet 48 are about the same since there is no flow of air that is forced through the incubator 20 by the operation of the fan 40. As such, obviously, upon detection of such deficiency, the alarm 66 would immediately notify the user of such fault condition so that appropriate action can be taken.

Figure 3C:
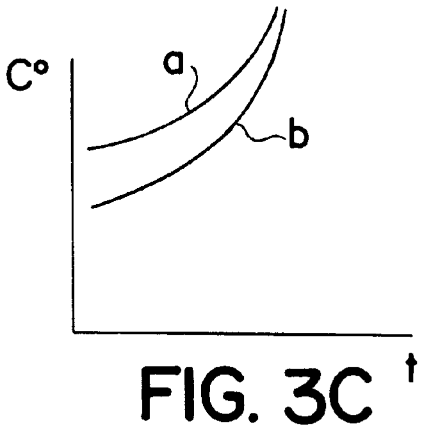

In FIG. 3C, a condition is detected that the incubator reached a steady state condition and then a run away heater occurred with the fan not running. As can be seen, the temperature sensors 50 and 52 both indicate a rapidly rising temperature in both the air inlet 46 and the air outlet 48. The condition would obviously cause an immediate alarm 66 and can also trigger a complete shut down of the incubator 20.

Figure 3D:
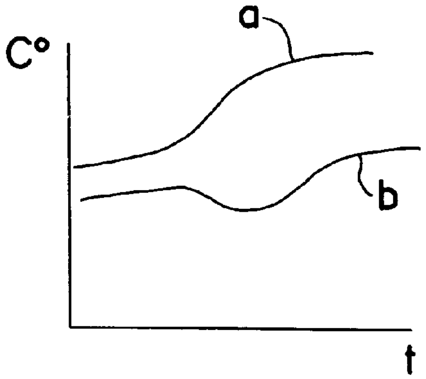

Next, in FIG. 3D, the curves indicates an open door or open handhole condition as the temperature in the air inlet 46 increases but the temperature in the air outlet 48 does not follow that increase in temperature providing an indication that the warm air is escaping outside the infant compartment 26. In such case, the use of the two temperature sensors 50 and 52 can detect the condition and may cause an alert to the user to advise that an opening is present and heat is being dissipated to the ambient atmosphere.

Figure 3E:
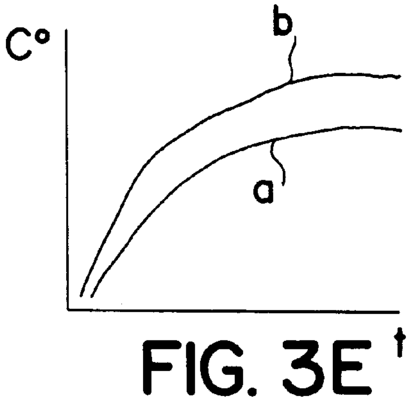

In FIG. 3E, the condition shown is where the fan 40 is running in the reverse direction such that the temperature rises to a higher temperature in the air outlet 48 than the air inlet 46. Again, a fault condition exists and which is detected by the particular location of the temperature sensors of the present invention.

Figure 3F:
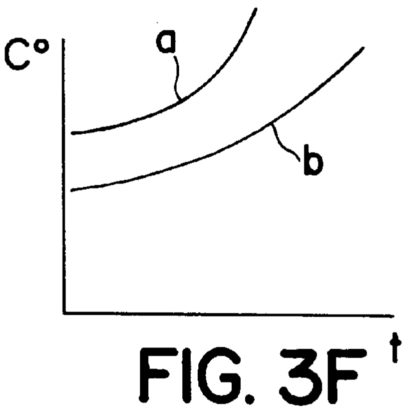

Finally, in FIG. 3F, a condition is shown where the incubator 20 reached a steady state condition and then experienced a run away heater such that the temperature in both the air inlet 46 and the air outlet 48 continues to rise, albeit at a lower rate that if the fan had also been inactivated as in the FIG. 3C condition.

Thus, by way of various examples, the use of positioning the temperature sensors in the air inlet and the air outlet of an infant incubator allows the overall system to provide a control of the heater system and yet also has the advantage of being able to recognize various fault conditions by a comparison of the sensed temperatures at those locations.

While the invention has been disclosed and described with respect to a single embodiment, it will become apparent that variations and modifications may be made therein, and it is therefore intended in the following claims to cover each variation and modification as falls within the true spirit and scope of the invention.

I claim:

1. An infant incubator for providing a controlled atmosphere for an infant, said incubator comprising an infant compartment for containing an infant, a heating system to provide a flow of warm air, an inlet for introducing the flow of warm air into said infant compartment to heat an infant contained therein and an outlet for exhausting air from said infant compartment, a temperature sensor providing a signal representative of the temperature of the air in said inlet and a temperature sensor providing a signal representative of the temperature of air in said outlet, a control system receiving the signals from said temperature sensors to compare said signals together to identify a fault condition of said heating system.

* * * * *